(12) United States Patent
Hagihara et al.

(10) Patent No.: US 12,114,981 B2
(45) Date of Patent: Oct. 15, 2024

(54) ELECTRODE-WIRING-EQUIPPED CLOTH MATERIAL

(71) Applicant: LINTEC CORPORATION, Tokyo (JP)

(72) Inventors: Yoshiaki Hagihara, Tokyo (JP); Shigeto Okuji, Tokyo (JP)

(73) Assignee: LINTEC CORPORATION, Tokyo (JP)

( * ) Notice: Subject to any disclaimer, the term of this patent is extended or adjusted under 35 U.S.C. 154(b) by 590 days.

(21) Appl. No.: 16/972,942

(22) PCT Filed: May 28, 2019

(86) PCT No.: PCT/JP2019/021125
§ 371 (c)(1),
(2) Date: Dec. 7, 2020

(87) PCT Pub. No.: WO2019/230730
PCT Pub. Date: Dec. 5, 2019

(65) Prior Publication Data
US 2021/0244332 A1 Aug. 12, 2021

(30) Foreign Application Priority Data

May 30, 2018 (JP) .................................. 2018-103874

(51) Int. Cl.
*A61B 5/27* (2021.01)
*A61B 5/00* (2006.01)
(Continued)

(52) U.S. Cl.
CPC ................ *A61B 5/27* (2021.01); *A61B 5/256* (2021.01); *D03D 1/0088* (2013.01); *D03D 15/00* (2013.01);
(Continued)

(58) Field of Classification Search
CPC .......... A61B 5/1116; A61B 2562/0209; A61B 2562/046; A61B 2562/222; A61B 5/256;
(Continued)

(56) References Cited

U.S. PATENT DOCUMENTS 6,341,504 B1 * 1/2002 Istook .................... D04B 21/18
66/172 E
9,554,465 B1 1/2017 Liu et al.
(Continued)

FOREIGN PATENT DOCUMENTS

CN 1985761 A 6/2007
CN 101437663 A 5/2009
(Continued)

OTHER PUBLICATIONS

The Extended European Search Report issued on Feb. 7, 2022.
International Search Report and Written Opinion for Application No. PCT/JP2019/021125 dated Aug. 6, 2019, 9 pages.

*Primary Examiner* — Jennifer A Steele
(74) *Attorney, Agent, or Firm* — Finch & Maloney PLLC

(57) ABSTRACT

Disclosed is an electrode-wiring-equipped cloth material including: a cloth material main body; an electrode section which is provided on a surface of or inside the cloth material main body and contains a conductive linear body; a wiring section which is provided adjacent to the electrode section on the surface of or inside the cloth material main body and contains a conductive linear body, in which cloth material at least one conductive linear body contained in the electrode section and at least on conductive linear body contained in the wiring section are the same single conductive linear body.

20 Claims, 7 Drawing Sheets

(51) Int. Cl.
*A61B 5/256* (2021.01)
*D03D 1/00* (2006.01)
*D03D 15/00* (2021.01)
*D03D 15/533* (2021.01)
*D03D 15/67* (2021.01)
*D04B 1/14* (2006.01)
*H05K 1/11* (2006.01)
*H05K 3/10* (2006.01)

(52) U.S. Cl.
CPC ........... *D03D 15/533* (2021.01); *D03D 15/67* (2021.01); *D04B 1/14* (2013.01); *H05K 1/11* (2013.01); *H05K 3/103* (2013.01); *A61B 5/6804* (2013.01); *A61B 2562/0209* (2013.01); *D05D 2303/40* (2013.01); *D10B 2401/16* (2013.01); *D10B 2403/02431* (2013.01)

(58) Field of Classification Search
CPC ...... A61B 5/6804; A61B 5/25; D03D 1/0088; D03D 15/533; D03D 15/56; D03D 15/275; D03D 15/593; D04B 1/14; D04B 21/00; D04B 1/123; D04B 1/18; A41D 1/002; A41D 31/185; D10B 2401/061; D10B 2401/16; D10B 2401/18; D10B 2403/02431
See application file for complete search history.

(56) References Cited

U.S. PATENT DOCUMENTS

| | | |
|---|---|---|
| 2007/0083096 A1 | 4/2007 | Paradiso |
| 2008/0170982 A1 | 7/2008 | Zhang et al. |
| 2010/0070008 A1* | 3/2010 | Parker ............... A61M 25/0009 607/116 |
| 2014/0343390 A1 | 11/2014 | Berzowska et al. |
| 2015/0359485 A1 | 12/2015 | Berg et al. |
| 2015/0376821 A1* | 12/2015 | McMaster ................ D04B 1/12 66/202 |
| 2016/0018274 A1 | 1/2016 | Seitz |
| 2017/0176167 A1* | 6/2017 | Keller ..................... G01L 1/225 |
| 2021/0388543 A1* | 12/2021 | Hagihara ............. D03D 15/533 |

FOREIGN PATENT DOCUMENTS

| | | | |
|---|---|---|---|
| CN | 203113015 U | 8/2013 | |
| CN | 107385623 A * | 11/2017 | ........... D03D 1/0088 |
| EP | 1506738 A1 * | 2/2005 | ......... A41D 13/1281 |
| JP | 2008523254 A | 7/2008 | |
| JP | 2010142413 A | 7/2010 | |
| JP | 2011015818 A * | 1/2011 | |
| JP | 2017070599 A | 4/2017 | |
| KR | 10-2008-0009043 A | 1/2008 | |
| WO | WO-0102052 A2 * | 1/2001 | ........... A61N 1/0452 |
| WO | 2007015710 A2 | 2/2007 | |
| WO | 2008009971 A2 | 1/2008 | |
| WO | WO-2017010236 A1 * | 1/2017 | ............ A41D 31/00 |
| WO | 2017140768 A1 | 8/2017 | |
| WO | 2018037855 A1 | 3/2018 | |

* cited by examiner

ELECTRODE-WIRING-EQUIPPED CLOTH MATERIAL

TECHNICAL FIELD

The present disclosure relates to an electrode-wiring-equipped cloth material.

BACKGROUND ART

Conventionally, as cloth materials utilized in wearable devices such as biological signal measuring devices, for example, cloth materials that include an electrode section for contact with a living body or sensor connection and a wiring section connected to the electrode section are employed (see, for example, Patent Document 1).

RELATED ART DOCUMENT

Patent Document

[Patent Document 1] Japanese Patent Application Laid-Open (JP-A) No. 2017-70599

SUMMARY OF INVENTION

Technical Problem

However, in such cloth materials having an electrode section and a wiring section, the electrode section and the wiring section are separately provided and connected via a connecting material (e.g., a solder or a conductive paste) or a connecting member (e.g., a caulking or a connector).

Particularly, in a case of arranging an electrode section for contact with a living body on a cloth material, since the wiring section is required to be coated with an insulating material for insulation while the electrode section for contact with a living body needs to be exposed, a constitution in which the electrode section and the wiring section are separately prepared and then connected via a connecting material or a connecting member tends to be adopted.

Accordingly, a connecting part of the electrode section and the wiring section is sometimes deteriorated due to repeated deformation (e.g., distortion, bending and/or elongation) of the cloth material. Specifically, for example, when the electrode section and the wiring sections are connected using a connecting material or a connecting member, repeated deformation of the cloth material causes cracking of the connecting material or the connecting member. A further deterioration of the connecting part leads to defective connection between the electrode section and the wiring section.

Moreover, a structure in which a conductive linear body contained in the electrode section and a conductive linear body contained in the wiring section are connected via a connecting member has higher durability against repeated deformation of the cloth material than a structure in which such linear-bodies are connected via a connecting material; however, since the connecting part of the former structure is less flexible, the utility value as a flexible cloth material is deteriorated.

In view of the above, an object of the disclosure is to provide an electrode-wiring-equipped cloth material which has flexibility as a cloth material and in which defective connection between an electrode section and a wiring section caused by repeated deformation is inhibited.

Solution to Problem

The above-described problems are solved by the following means.

<1> An electrode-wiring-equipped cloth material including:
 a cloth material main body:
 an electrode section that is provided on a surface of or inside the cloth material main body and that contains a conductive linear body; and
 a wiring section that is provided adjacent to the electrode section on the surface of or inside the cloth material main body and that contains a conductive linear body,
 wherein at least one conductive linear body contained in the electrode section and at least one conductive linear body contained in the wiring section are the same single conductive linear body.

<2> The electrode-wiring-equipped cloth material according to <1>, which has elasticity.

<3> The electrode-wiring-equipped cloth material according to <2>, wherein, when the electrode-wiring-equipped cloth material is elongated at 50% of a maximum elongation, the rate of change in resistance of the wiring section is 10% or less with respect to the resistance of the wiring section prior to the elongation of the electrode-wiring-equipped cloth material.

<4> The electrode-wiring-equipped cloth material according to any one of <1> to <3>, wherein, in the electrode section, a part of the conductive linear body is restrained by a yarn of the cloth material main body.

<5> The electrode-wiring-equipped cloth material according to <4>, wherein, in the electrode section, the conductive linear body is woven, knitted or embroidered into the cloth material main body, or the electrode section is sewn on with the conductive linear body.

<6> The electrode-wiring-equipped cloth material according to any one of <1> to <5>, wherein the electrode section is provided on the surface of the cloth material main body.

<7> The electrode-wiring-equipped cloth material according to <6>, wherein the electrode section is an electrode section for contact with a living body.

<8> The electrode-wiring-equipped cloth material according to any one of <1> to <7>, wherein, in the wiring section, a part of the conductive linear body is restrained by a yarn of the cloth material main body.

<9> The electrode-wiring-equipped cloth material according to <8>, wherein, in the wiring section, the conductive linear body is woven, knitted or embroidered into the cloth material main body, or the wiring section is sewn on with the conductive linear body.

<10> The electrode-wiring-equipped cloth material according to any one of <1> to <9>, wherein the wiring section is provided inside the cloth material main body.

<11> The electrode-wiring-equipped cloth material according to any one of <1> to <10>, wherein the conductive linear-bodies contained in the electrode section and the wiring section are conductive linear-bodies including a carbon nanotube yarn.

Effects of Invention

According to the disclosure, an electrode-wiring-equipped cloth material which has flexibility as a cloth material and in which defective connection between an electrode section and a wiring section caused by repeated deformation is inhibited can be provided.

DESCRIPTION OF EMBODIMENTS

Mode for Carrying Out the Invention

Figure 1:
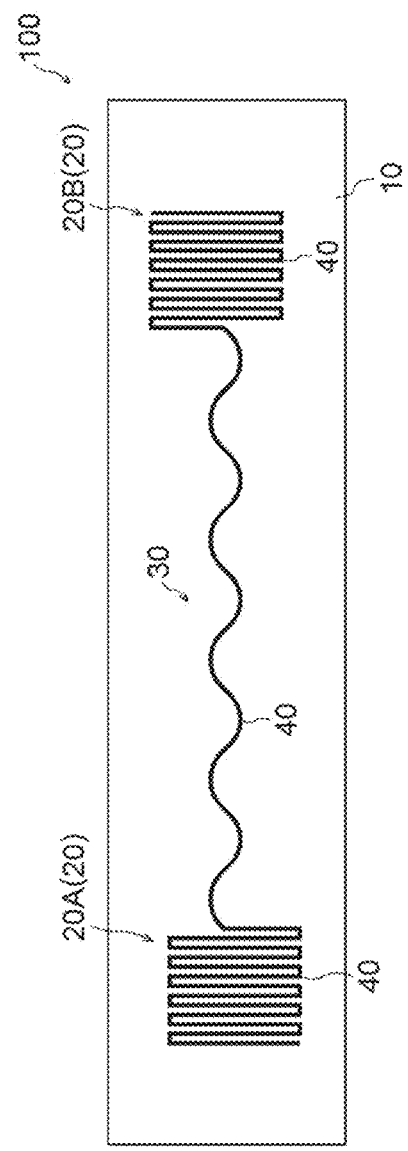
FIG. 1 is a schematic plan view that illustrates the electrode-wiring-equipped cloth material according to the present embodiment.

One exemplary embodiment of the disclosure is described below in detail.

In the present specification, the same symbols are assigned to members having substantially the same functions in all of the drawings, and redundant descriptions thereof may be omitted.

Those numerical ranges that are expressed with "to" each denote a range that includes the numerical values stated before and after "to" as the minimum value and the maximum value, respectively.

In the stepwise range of numerical values shown in this specification, an upper limit value or a lower limit value disclosed in a certain range of numerical values may be replaced with an upper limit value or a lower limit value of another stepwise range of numerical values. In addition, in the range of numerical values disclosed in this specification, an upper limit value or a lower limit value disclosed in a certain range of numerical values may be replaced with values shown in examples.

In this specification, a term "step" not only includes an independent step, but also includes a step, in a case where the step may not be distinguished from the other step, as long as the expected object of the step is achieved.

The electrode-wiring-equipped cloth material according to the present embodiment includes: a cloth material main body: an electrode section which is provided on a surface of or inside the cloth material main body and contains a conductive linear body; and a wiring section which is provided adjacent to the electrode section on the surface of or inside the cloth material main body and contains a conductive linear body.

At least one conductive linear body contained in the electrode section and at least one conductive linear body contained in the wiring section are the same single conductive linear body.

The term "the same single conductive linear body" used herein also encompasses a linear body formed by joining conductive linear-bodies at their ends by knotting, twisting or the like without the use of a connecting material (e.g., a solder or a conductive paste) or a connecting member (e.g., a caulking or a connector) other than the linear body.

In the electrode-wiring-equipped cloth material according to the present embodiment, at least one conductive linear body contained in the electrode section and at least one conductive linear body contained in the wiring section are the same single conductive linear body. In other words, since the electrode section and the wiring section are connected via the same single conductive linear body, deterioration of the connecting part of the electrode section and the wiring section, which is caused by repeated deformation (e.g., distortion, bending and/or elongation) of the cloth material, is suppressed. As a result, defective connection between the electrode section and the wiring section is inhibited. Moreover, the flexibility of the cloth material is maintained as well.

The term "cloth material main body" used herein refers to a cloth material on which a conductive linear body(ies) is/are to be provided.

An expression "an electrode section or a wiring section is provided on a surface of a cloth material main body" used herein means that the electrode section or the wiring section (i.e., conductive linear body) is provided on a cloth material layer constituting front and back surfaces of the cloth material main body (the term "cloth material layer" also encompasses a cloth material layer partially constituting the front and back surfaces). In other words, the expression "an electrode section or a wiring section is provided on a surface of a cloth material main body" means that the electrode section or the wiring section (i.e., conductive linear body) is arranged in a state where the conductive linear body constituting the electrode section or the wiring section is at least partially exposed from the cloth material main body.

An expression "an electrode section or a wiring section is provided inside a cloth material main body" used herein means that the electrode section or the wiring section (i.e., conductive linear body) is provided in an inner layer of the cloth material main body, for example, in a cloth material layer constituting the inner layer of the cloth material main body or between such cloth material layers.

The phrase "at least one conductive linear body contained in the electrode section and at least one conductive linear body contained in the wiring section are the same single conductive linear body" means that the wiring section contains at least one conductive linear body extending from the electrode section (in other words, the electrode section contains at least one conductive linear body extending from the wiring section).

One example of the electrode-wiring-equipped cloth material according to the present embodiment is described below referring to the drawings.

Figure 2:
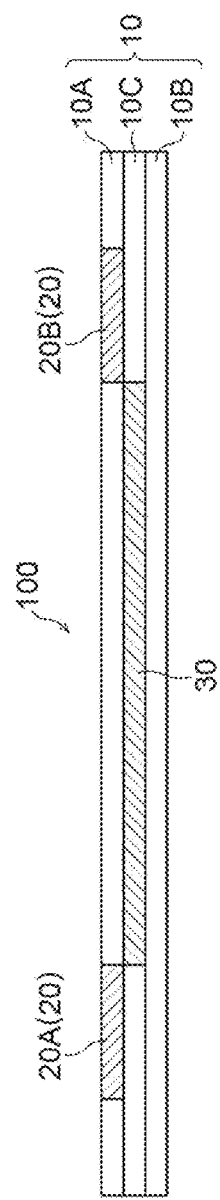
FIG. 2 is a schematic cross-sectional view that illustrates the electrode-wiring-equipped cloth material according to the present embodiment.

As illustrated in FIGS. 1 and 2, an electrode-wiring-equipped cloth material 100 according to the present embodiment includes: a cloth material main body 10: electrode sections 20; and a wiring section 30.

(Cloth Material Main Body)

The cloth material main body 10 is constituted by three cloth material layers of, for example, a surface cloth material layer 10A constituting a front surface, a back-surface cloth material layer 10B constituting a back surface, and an intermediate cloth material layer 10C provided between the surface cloth material layer 10A and the back-surface cloth material layer 10B.

Other than such a three-cloth-material-layer constitution, the cloth material main body 10 may also be constituted by, for example, one, two, or four or more cloth material layers.

The cloth material main body 10 having multiple layers composed of two or more cloth material layers may be produced by, for example, a method of preparing the respective cloth material layers and then sewing together the thus prepared cloth material layers, or the cloth material main body 10 having multiple layers may be produced at once using a weaving/knitting machine.

Representative examples of the cloth material main body 10 include-woven/knitted fabrics. The cloth material main body 10 may be a nonwoven fabric as well.

Examples of the woven/knitted fabrics include-woven fabrics obtained by plain weaving, twill weaving, satin weaving, well-known applied weaving or the like; and knitted fabrics obtained by weft knitting, warp knitting, lace knitting, well-known applied knitting or the like.

Yarns (linear-bodies) constituting the cloth material main body 10 are insulating yarns. The term "insulating yarns" used herein refers to yarns having a line resistance of not less than $1.0 \times 10^6$ Ω/cm. The line resistance of the insulating yarns is measured by the same method as the below-described line resistance of conductive linear-bodies.

Examples of the yarns (linear-bodies) constituting the cloth material main body 10 include yarns of well-known fibers.

The yarns of well-known fibers may be synthetic fiber yarns or natural fiber yarns.

Examples of the synthetic fiber yarns include yarns of polyurethane fibers, polyester fibers (e.g., polyalkylene terephthalate fibers and polyarylate fibers), polyamide fibers (e.g., nylon 6 fibers, nylon 66 fibers, and nylon 46 fibers), aromatic polyamide fibers (e.g., fibers of copolymers of para-phenylene terephthalamide and aromatic ether), vinylon fibers, polyvinyl chloride fibers, polyolefin fibers (e.g., rayon fibers and ultrahigh-molecular-weight polyethylene fibers), polyoxymethylene fibers, sulfone-based fibers (e.g., para-phenylene sulfone fibers and polysulfone fibers), polyether ether ketone fibers, polyether imide fibers, polyimide fibers and the like.

Examples of the natural fiber yarns include fiber yarns of cotton, silk, hemp, wool and the like.

The cloth material main body 10 is desirably an elastic cloth material. In other words, it is desired that the electrode-wiring-equipped cloth material 100 has elasticity. Particularly, when the electrode-wiring-equipped cloth material 100 has elasticity, the connecting parts of the electrode sections 20 and the wiring section 30 are deteriorated by repeated elongation and contraction, which is likely to cause defective connection. However, by adopting the constitution of the electrode-wiring-equipped cloth material 100 according to the present embodiment, defective connection between the electrode sections 20 and the wiring section 30 is inhibited.

The cloth material main body 10 having elasticity can be realized by applying a woven/knitted fabric utilizing an elastic yarn.

Examples of the elastic yarn include covered yarns (single-covered yarns and double-covered yarns) obtained by winding a non-elastic yarn(s) in a coil form on the outer circumference of an elastic yarn: core-spun yarns obtained by spinning and intertwisting an elastic yarn with a non-elastic yarn: air-entangled covered yarns obtained by winding a non-elastic yarn on the outer circumference of an elastic yarn using an air pressure nozzle; and twisted yarns obtained by twisting an elastic yarn with a non-elastic yarn.

Examples of the elastic yarn also include yarns of fibers showing so-called rubber-like elasticity, such as polyurethane elastic fibers, polyester elastic fibers and polyamide elastic fibers.

Examples of the non-elastic yarn include yarns of synthetic fibers (e.g., polyester fibers, polyamide fibers, acryl fibers, polypropylene fibers, and rayon fibers) and natural fibers (e.g., fibers of cotton, silk, hemp, wool and the like).

(Electrode Section and Conductive Section)

The electrode sections 20 include a first electrode section 20A and a second electrode section 20B. In accordance with the intended purpose, one or three or more electrode sections 20 may be provided.

For example, in cases where the electrode-wiring-equipped cloth material 100 is utilized in a wearable device such as a biological signal measuring device, it is desired that at least one of the electrode sections 20 is used as an electrode section for contact with a living body. Specifically, for example, of the two electrode sections 20, the first electrode section 20A is used as an electrode section for contact with a living body, while the second electrode section 20B is used as an electrode section for connecting other instrument (e.g., for connecting a transmission device, or for connecting an external instrument). The first electrode section 20A is not particularly restricted to be an electrode section for contact with a living body, and it may also be used as an electrode section for sensor connection. Further, when three or more electrode sections 20 are provided, two or more of the electrode sections 20) may be used as an electrode section for contact with a living body and an electrode section for sensor connection.

The electrode sections 20 are provided in the surface cloth material layer 10A of the cloth material main body 10. In other words, the electrode sections 20 are provided on the surface of the cloth material main body 10.

The electrode sections 20 may also be provided in the intermediate cloth material layer 10C of the cloth material main body 10. In other words, the electrode sections 20 may be provided inside the cloth material main body 10.

For example, the electrode section for contact with a living body (i.e., the conductive linear body 40 constituting the electrode section for contact with a living body) is required to be exposed from the electrode-wiring-equipped cloth material 100. On the other hand, the electrode section for sensor connection and the electrode section for connecting other instrument (e.g., for connecting a transmission device, or for connecting an external instrument) (i.e., the conductive linear-bodies 40) constituting the electrode section for sensor connection and the electrode section for connecting other instrument) are not required to be exposed from the electrode-wiring-equipped cloth material 100. This is because, even when the electrode section for sensor connection and the electrode section for connecting other instrument are provided inside the cloth material main body 10, they can be connected by a pin electrode or the like.

Meanwhile, a single wiring section 30 is provided adjacent to the first electrode section 20A and the second electrode section 20B. In other words, a single wiring section 30 is provided in such a manner to link the first electrode section 20A and the second electrode section 20B. Depending on the number of the electrode sections 20, two or more wiring sections 30 may be provided.

The wiring section 30 is provided inside the cloth material main body 10. Specifically, the wiring section 30 can be provided inside the cloth material main body 10 by, for example, providing the wiring section 30 in the intermediate cloth material layer 10C which is an inner cloth material layer (including a cloth material layer partially serving as an inner layer) of the cloth material main body 10 constituted by three cloth material layers. Further, for example, in the cloth material main body 10 constituted by two cloth material layers, the conductive linear body 40 serving as the wiring section 30 may be provided between the two cloth material layers.

The wiring section 30 may also be provided on a surface of the cloth material main body 10. For example, the wiring section 30 may be provided on the surface cloth material layer 10A or the back-surface cloth material layer 10B of the cloth material main body 10 constituted by three cloth material layers. It is noted here, however, that the wiring section 30 is desirably provided inside the cloth material main body 10 from the standpoint of attaining insulation from the outside by the cloth material main body 10.

In the electrode sections 20 and/or the wiring section 30, at least a part of each conductive linear body 40 is restrained by a yarn of the cloth material main body 10. This mode is preferred from the standpoint that the conductive linear body 40, which functions as a conductive material of the electrode sections 20 or the wiring section 30, can also be used as a means for immobilizing the electrode sections 20 or the wiring section 30 with the cloth material main body 10. The conductive linear body 40 restrained to the cloth material main body 10 may be the same single conductive linear body 40 contained in both the electrode sections 20 and the wiring section 30, or different conductive linear body 40 contained in only either the electrode sections 20 or the wiring section 30. It is noted here that, in the electrode sections 20 or the wiring section 30, the conductive linear body 40 does not have to be restrained by a yarn of the cloth material main body 10. For example, in cases where the wiring section 30 or the electrode sections 20 are immobilized with the cloth material main body 10 by an adhesive, or in cases where the wiring section 30 or the electrode sections 20 are sewn on the cloth material main body 10 using an insulating yarn, the wiring section 30 or the electrode sections 20 can be immobilized on the cloth material main body 10 even if the conductive linear body 40 is not restrained by a yarn of the cloth material main body 10.

For example, a rectangular region where the conductive linear body 40 is provided in a manner of being repeatedly bent or curved at 180° is formed. The rectangular region is formed by partially restraining the conductive linear body 40 using a yarn of the surface cloth material layer 10A of the cloth material main body 10. This rectangular region is defined as a planar electrode section 20.

A region where the conductive linear body 40 is spirally provided may be adopted as one electrode section 20. Further, an arbitrary planar shape (e.g., a polygonal shape or a circular shape) in which the conductive linear body 40 is provided in a bent or curved manner may also be adopted as one electrode section 20.

Meanwhile, the conductive linear-bodies 40 of the electrode sections 20 (the first electrode section 20A and the second electrode section 20B) are extended in an undulating shape between the electrode sections 20 to form a region having an undulating shape. The region having an undulating shape is formed by partially restraining the conductive linear-bodies 40 using a yarn of the intermediate cloth material layer 10C of the cloth material main body 10. This region having an undulating shape is defined as the wiring section 30).

A linear-shaped region where the conductive linear body 40 is provided in a linear shape may be adopted as the wiring section 30. However, from the standpoint of inhibiting defective connection between the electrode sections 20 and the wiring section 30 caused by elongation of the electrode-wiring-equipped cloth material 100, the wiring region 30 is desirably a region having an undulating shape (i.e., a region where the conductive linear body 40 is provided in an undulating shape).

Figure 3:
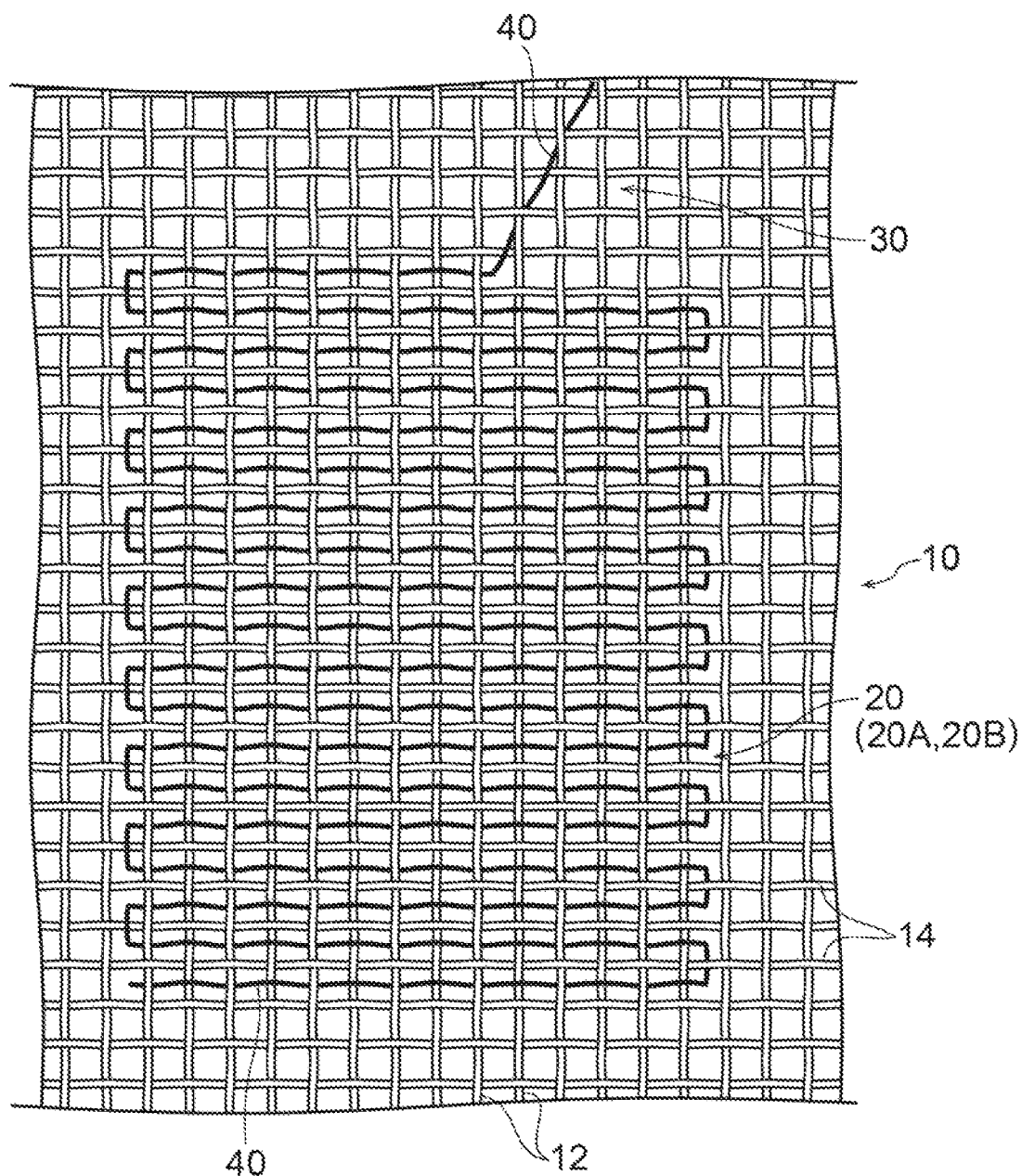
FIG. 3 is a schematic plan view that illustrates one example where a conductive linear body is woven in the electrode-wiring-equipped cloth material according to the present embodiment.

Specifically, when the cloth material main body 10 is a woven fabric, as illustrated in FIG. 3, from the standpoint of simultaneously forming the electrode sections 20 and/or the wiring section 30 at the time of preparing the woven fabric as the cloth material main body 10, as well as from the standpoint of improving the integrity of the cloth material main body 10 with the electrode sections 20 and/or the wiring section 30, it is preferred to constitute the electrode sections 20 and/or the wiring section 30 by weaving the conductive linear body 40 into a woven structure of a woven fabric obtained by weaving a warp yarn and a weft yarn.

Figure 4:
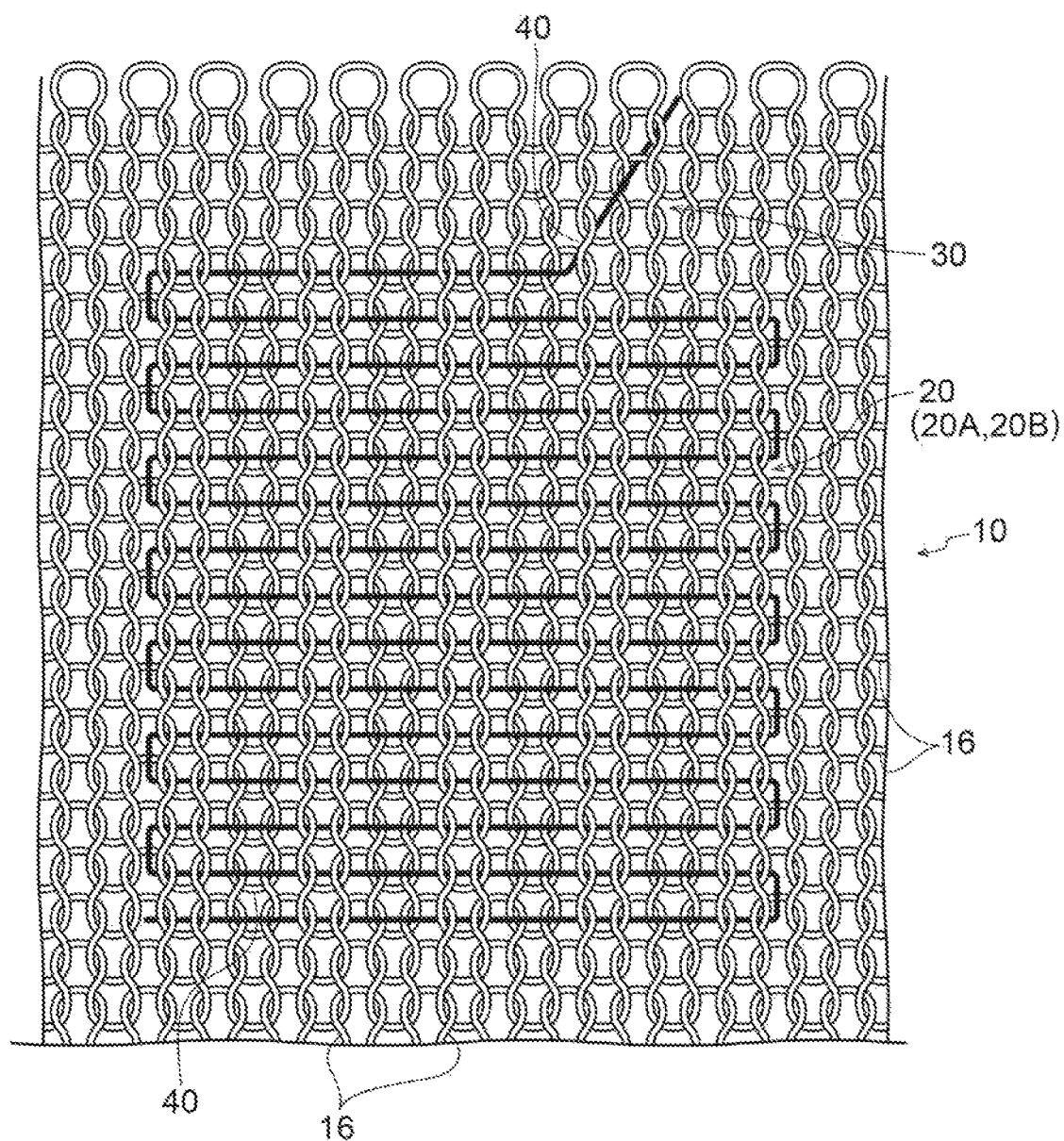
FIG. 4 is a schematic plan view that illustrates one example where a conductive linear body is knitted in the electrode-wiring-equipped cloth material according to the present embodiment.

When the cloth material main body 10 is a knitted fabric, as illustrated in FIG. 4, from the standpoint of simultaneously forming the electrode sections 20 and/or the wiring section 30 at the time of preparing the cloth material main body 10 by knitting, as well as from the standpoint of improving the integrity of the cloth material main body 10 with the electrode sections 20 and/or the wiring section 30, it is preferred to constitute the electrode sections 20 and/or the wiring section 30 by knitting the conductive linear body 40 in any of the above-described shapes into a knitted structure of a knitted fabric obtained by knitting a yarn in the form of loops. For the knitting of the conductive linear body 40 into a knitted structure of a knitted fabric, for example, parallel knitting, plating knitting, or inlay knitting can be employed. FIG. 4 illustrates an example where the conductive linear body 40 is knitted by inlay knitting.

Figure 5:
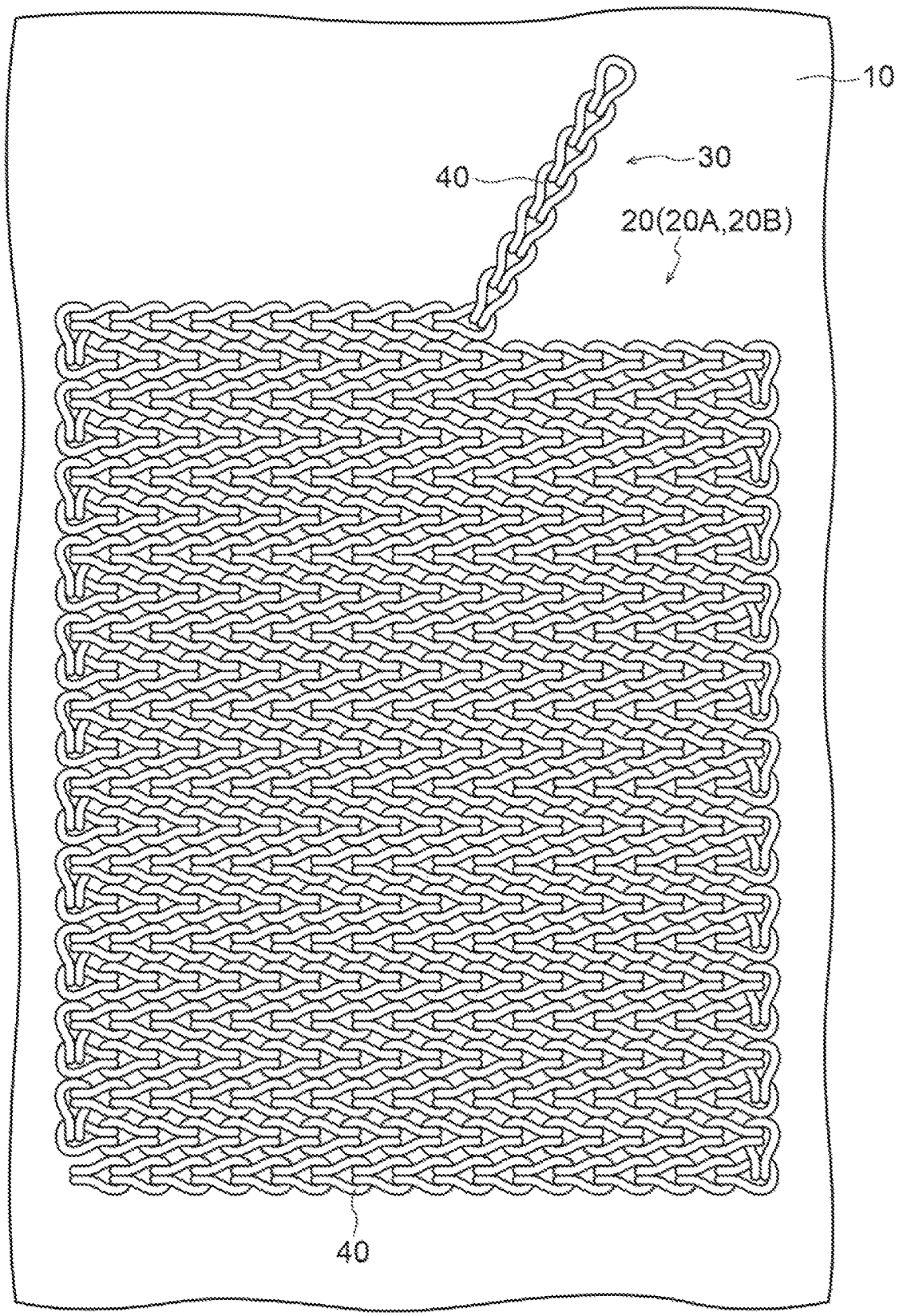
FIG. 5 is a schematic plan view that illustrates one example where a conductive linear body is embroidered in the electrode-wiring-equipped cloth material according to the present embodiment.

Further, as illustrated in FIG. 5, from the standpoint of also simultaneously immobilizing the electrode sections 20 and/or the wiring section 30 on the cloth material main body 10 at the time of forming the electrode sections 20 and/or the wiring section 30, it is preferred to constitute the electrode sections 20 and/or the wiring section 30 by embroidering the conductive linear body 40 in any of the above-described shapes on the cloth material main body 10. As an embroidering method, for example, a well-known stitching technique such as running stitch, couching stitch, back stitch, chain stitch or outline stitch can be employed. FIG. 5 illustrates an example where the conductive linear body 40 is embroidered by chain stitching.

Moreover, from the standpoint of using a common conductive linear body 40 for both constituting and immobilizing the electrode sections 20 and/or wiring section 30, it is preferred to immobilize the electrode sections 20 and/or the wiring section 30 on the cloth material main body 10 by sewing them with the conductive linear body 40.

Examples of such a mode of immobilizing the electrode sections 20 and/or the wiring section 30 by sewing them with the conductive linear body 40 include a mode in which the electrode section(s) 20 and the wiring section 30 are continuously formed from a woven fabric obtained by weaving the conductive linear body 40 or a knitted fabric obtained by knitting the conductive linear body 40 and the thus formed electrode section(s) 20 and wiring section 30 are sewn on the cloth material main body 10 with the conductive linear body 40.

In FIG. 3. "12" represents the warp yarn constituting the cloth material main body 10 (knitted fabric), and "14" represents the weft yarn constituting the cloth material main body 10 (knitted fabric). In FIG. 4. "16" represents the yarn constituting the cloth material main body 10 (knitted fabric).

In addition to the mode in which the electrode section(s) 20 and the wiring section 30 are constituted by the same single conductive layer-body 40, the electrode section(s) 20 and the wiring section 30 may also be constituted by two or more of the same conductive linear-bodies.

Further, the electrode section(s) 20 and the wiring section 30 may each be constituted by plural conductive linear-bodies 40 as well. However, among the plural conductive linear-bodies 40, at least one conductive linear body 40 constitutes both the electrode section 20 and the wiring section 30.

When plural electrode sections 20 are provided, at least one conductive linear body contained in at least one of the electrode sections 20 and at least one conductive linear body contained in the wiring section 30 provided adjacent to the at least one of the electrode sections 20 are the same single conductive linear body 40.

In cases where an elastic yarn is employed as a yarn constituting the cloth material main body 10, it is desirable to weave or knit a conductive linear body into the cloth material main body 10 while forming a woven/knitted fabric with the elastic yarn being in an elongated state.

(Conductive Linear Body)

The conductive linear-bodies constituting the electrode section 20 and the wiring section 30 are not particularly restricted as long as they are electrically conductive, and examples thereof include metal wire-containing linear-bodies and conductive yarn-containing linear-bodies. The conductive linear body 40 may be a linear body containing both a metal wire and a conductive yarn (e.g., a linear body obtained by twisting a metal wire and a conductive yarn).

Metal wire-containing linear-bodies and conductive yarn-containing linear-bodies both have high conductivity and high electrical conductivity: therefore, the resistance of the electrode section 20 and that of the wiring section 30 are easily reduced by applying such a linear body as the conductive linear body 40.

Examples of the metal wire include-wires containing a metal, such as copper, aluminum, tungsten, iron, molybdenum, nickel, titanium, silver or gold, or an alloy of two or more metals (e.g., steels such as stainless steel and carbon steel, brass, phosphor bronze, zirconium-copper alloy, beryllium-copper, iron-nickel, nichrome, nickel-titanium, kanthal, hastelloy, and rhenium-tungsten). The metal wire may be plated with tin, zinc, silver, nickel, chromium, a nickel-chromium alloy, a solder or the like, and the surface of the metal wire may be covered with any of the below-described carbon materials and polymers.

Examples of the metal wire also include metal wires covered with a carbon material. When the metal wire is covered with a carbon material, metal corrosion is inhibited.

Examples of the carbon material covering the metal wire include amorphous carbons, such as carbon black, activated charcoal, hard carbon, soft carbon, mesoporous carbon, and carbon fibers: graphite: fullerene: graphene; and carbon nanotubes.

Meanwhile, the conductive yarn-containing linear-bodies may be linear-bodies composed of a single conductive yarn, or linear-bodies obtained by twisting plural conductive yarns. The conductive yarn-containing linear-bodies may also be linear-bodies obtained by twisting a conductive yarn and an insulating yarn. Such conductive yarn-containing linear-bodies are advantageous in that they have higher flexibility and are thus less likely to be broken when woven, knitted or embroidered into the cloth material main body 10 or sewn onto the cloth material main body 10 as compared to metal wire-containing linear-bodies. Examples of the conductive yarn include yarns containing conductive fibers (e.g., metal fibers, carbon fibers, and fibers of ion-conductive polymers); yarns containing conductive fine particles (e.g., carbon nanoparticles); yarns on which a metal (e.g., copper, silver, or nickel) has been plated or vapor-deposited; and yarns impregnated with a metal oxide.

Examples of particularly preferred conductive yarn-containing linear-bodies include linear-bodies that contain a yarn containing carbon nanotubes as carbon nanoparticles (carbon nanotube yarn) (such linear-bodies are hereinafter also referred to as "carbon nanotube linear-bodies").

A carbon nanotube linear body can be obtained by, for example drawing carbon nanotubes into a sheet form from an edge of a carbon nanotube forest (i.e., a growth body sometimes referred to as "array", which is produced by growing plural carbon nanotubes on a substrate such that the carbon nanotubes are vertically oriented with respect to the substrate), bundling the thus drawn carbon nanotube sheet, and then twisting the resulting carbon nanotube bundle. In this production method, a ribbon-form carbon nanotube linear body is obtained when no torsion is added during the twisting, while a thread-form linear body is obtained when torsion is added during the twisting. The ribbon-form carbon nanotube linear body is a linear body that does not have a structure in which an aggregate of plural carbon nanotubes is distorted. In addition, a carbon nanotube linear body can also be obtained by, for example, spinning from a dispersion of carbon nanotubes. The production of a carbon nanotube linear body by spinning can be performed in accordance with, for example, the method disclosed in US Patent Publication No. 2013/0251619 (JP-A No. 2011-253140). From the standpoint of obtaining a carbon nanotube linear body having a uniform diameter, it is desirable to use a thread-form carbon nanotube linear body and, from the standpoint of obtaining a high-purity carbon nanotube linear body, it is preferred to obtain a thread-form carbon nanotube linear body by twisting a carbon nanotube sheet. The carbon nanotube linear body may also be a linear body in which two or more carbon nanotube linear-bodies are twisted together.

The carbon nanotube linear body may also be a linear body that contains carbon nanotubes and a conductive material other than carbon nanotubes, such as a metal, a conductive polymer or graphene (such a linear body is hereinafter also referred to as "composite linear body."). In a composite linear body, the conductivity can be easily improved while maintaining the above-described characteristics of a carbon nanotube linear body.

Examples of the composite linear body include, as linear-bodies containing carbon nanotubes and a metal: (1) a composite linear body obtained by, in the process of drawing carbon nanotubes into a sheet form from an edge of a carbon nanotube forest, bundling the thus drawn carbon nanotube sheet and the twisting the resulting carbon nanotube bundle to obtain a carbon nanotube linear body, allowing a surface of the carbon nanotube forest, sheet or bundle or the twisted linear body to carry a simple metal or a metal alloy by vapor deposition, ion plating, sputtering, wet plating or the like: (2) a composite linear body obtained by twisting a bundle of carbon nanotubes together with a linear body of a simple metal, a linear body of a metal alloy or a composite linear body; and (3) a composite linear body obtained by twisting a linear body of a simple metal, a linear body of a metal alloy or a composite linear body together with a carbon nanotube linear body or another composite linear body. In the composite linear body of (2), at the time of twisting the bundle of the carbon nanotubes, the carbon nanotubes may be allowed to carry a metal in the same manner as in the composite linear body of (1). Further, the composite linear body of (3) is a composite linear body obtained by knitting two linear-bodies: however, as long as at least one linear body of a simple metal, linear body of a metal alloy or composite linear body is included, the composite linear body of (3) may be obtained by knitting together three or more of carbon nanotube linear-bodies, linear-bodies of a simple metal, linear bodies of a metal alloy, or composite linear-bodies.

Examples of the metals of these composite linear-bodies include simple metals, such as gold, silver, copper, iron, aluminum, nickel, chromium, tin and zinc; and alloys containing at least one of these simple metals (e.g., copper-nickel-phosphorus alloys and copper-iron-phosphorus-zinc alloys).

Among these conductive linear-bodies 40, carbon nanotube yarn-containing conductive linear-bodies (particularly, conductive linear-bodies containing only carbon nanotube yarns, and conductive linear-bodies containing carbon nanotube yarns and a non-metallic conductive material) are preferred.

For example, yarns whose surfaces are plated or vapor-deposited with a metal (e.g., copper, silver or nickel) and yarns impregnated with a metal oxide have low durability since the metal or the metal oxide is easily cracked due to repeated elongation and contraction. In this respect, carbon nanotube linear-bodies have strong resistance to bending, and the resistance value of the wiring section is thus unlikely to change even when the electrode-wiring-equipped cloth material 100 is subjected to repeated elongation and contraction. In addition, carbon nanotube linear-bodies are also advantageous in that they have high corrosion resistance.

The line resistance of the conductive linear body 40 is preferably from $5.0 \times 10^{-3}$ Ω/cm to $1.0 \times 10^3$ Ω/cm, more preferably from $1.0 \times 10^{-2}$ Ω/cm to $5.0 \times 10^2$ Ω/cm.

The line resistance of the conductive linear body 40 is measured as follows. First, both ends of the conductive linear body 40 are coated with a silver paste, and the resistance of the part between the silver paste-coated ends is measured to determine the resistance value (unit: (2) of the conductive linear body 40. Then, the line resistance of the conductive linear body 40 is calculated by dividing the thus obtained resistance value by the distance (cm) between the silver paste-coated ends.

(Other Properties)

When the electrode-wiring-equipped cloth material 100 is elongated at 50% of a maximum elongation, the rate of change in the resistance of the wiring section 30 is desirably 10% or less (preferably 5% or less) with respect to the resistance of the wiring section 30 prior to the elongation of the electrode-wiring-equipped cloth material 100.

In cases where only a single electrode section 20 is provided on one end of the wiring section 30 to be measured in such a manner that these sections share the same single conductive linear body 40, the "resistance of the wiring section 30" means the resistance between the electrode section 20 and the other end of the wiring section 30 (the end of the wiring section 30 on the side that is not adjacent to the electrode section 20). In this case, the elongation direction of the electrode-wiring-equipped cloth material 100 is defined as the extending direction of an imaginary line that connects the center of the single electrode section 20 and the other end of the wiring section 30.

Further, in cases where two electrode sections 20 (e.g., the first electrode section 20A and the second electrode section 20B) are provided at the respective ends of the wiring section 30 to be measured in such a manner that these sections share the same single conductive linear body 40, the "resistance of the wiring section 30" means the resistance between the two electrode sections 20. In this case, the elongation direction of the electrode-wiring-equipped cloth material 100 is defined as the extending direction of an imaginary line that connects the centers of the two electrode sections 20.

With the rate of change in the resistance of the wiring section 30 being small, the operational stability of an elastic device such as a wearable device (e.g., a biological signal measuring device) against elongation of the cloth material is improved. Also in those applications where the electrode-wiring-equipped cloth material 100 is elongated at a high degree, from the standpoint of improving the operational stability of a device, the rate of change in the resistance of the wiring section 30 is desirably 10% or less (preferably 5% or less) when the electrode-wiring-equipped cloth material 100 is elongated to the maximum elongation.

In order to control the rate of change in the resistance of the wiring section 30 to be 10% or less under elongation at 50% of the maximum elongation or under the maximum elongation, for example, the above-described method in which an elastic yarn is used as a yarn constituting the cloth material main body 10 and a conductive linear body is woven or knitted into the cloth material main body 10 while forming a woven/knitted fabric with the elastic yarn being in an elongated state can be employed.

The rate of change in the resistance of the wiring section 30 is measured as follows.

While continuously measuring the resistance of the wiring section 30, a portion of the electrode-wiring-equipped cloth material 100 that corresponds to the wiring section is elongated to the maximum elongation at a rate of 1 mm/s and subsequently allowed to contract back to the original state at the same rate. In this process, the resistance value RA (Ω) of the wiring section 30 prior to the elongation of the electrode-wiring-equipped cloth material 100 and the resistance value RB (Ω) of the wiring section 30 at a prescribed elongation degree (e.g., at 50% of the maximum elongation or at the maximum elongation (100%)) of the electrode-wiring-equipped cloth material 100 are measured.

Then, the rate of change in the resistance of the wiring section 30 is calculated using the following equation: Rate of change in resistance of wiring section 30=(RB−RA)/RA× 100. It is noted here that the rate of change in the resistance of the wiring section 30 is an absolute value.

The "maximum elongation" of the electrode-wiring-equipped cloth material 100 is defined as follows.

The maximum elongation of the electrode-wiring-equipped cloth material 100 is a length at which the electrode-wiring-equipped cloth material 100 cannot be elongated any further when elongated with an appropriate tension. In other words, a length of the electrode-wiring-equipped cloth material 100 elongated with a tension that stops the elongation is defined as the maximum elongation of the electrode-wiring-equipped cloth material 100.

MODIFICATION EXAMPLES

The electrode-wiring-equipped cloth material 100 according to the present embodiment is not restricted to the above-described modes and may be modified or improved. Modification examples of the electrode-wiring-equipped cloth material 100 according to the present embodiment are described below: In the followings, with regard to the electrode-wiring-equipped cloth material 100 according to the present embodiment, the same members as those of the above-described modes are assigned with the same symbols in the drawings, and descriptions thereof are omitted or simplified.

First Modification Example

Figure 6:
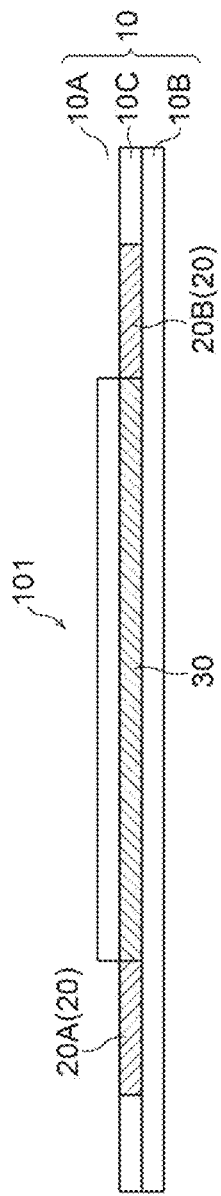
FIG. 6 is a schematic cross-sectional view that illustrates a first modification example of the electrode-wiring-equipped cloth material according to the present embodiment.

The electrode-wiring-equipped cloth material 100 according to the present embodiment may be, for example, an electrode-wiring-equipped cloth material 101 illustrated in FIG. 6. Specifically, as illustrated in FIG. 6, the electrode-wiring-equipped cloth material 101 has a three-layered cloth material main body 10, which includes a surface cloth material layer 10A, an intermediate cloth material layer 10C and a back-surface cloth material layer 10B. In the intermediate cloth material layer 10C, electrode sections 20 (a first electrode section 20A and a second electrode section 20B) each containing a conductive linear body 40 are provided along with a wiring section 30 containing the respective conductive linear-bodies 40 extending from the electrode sections 20. Only the wiring section 30 provided in the intermediate cloth material layer 10C is covered with the surface cloth material layer 10A.

Second Modification Example

Figure 7:
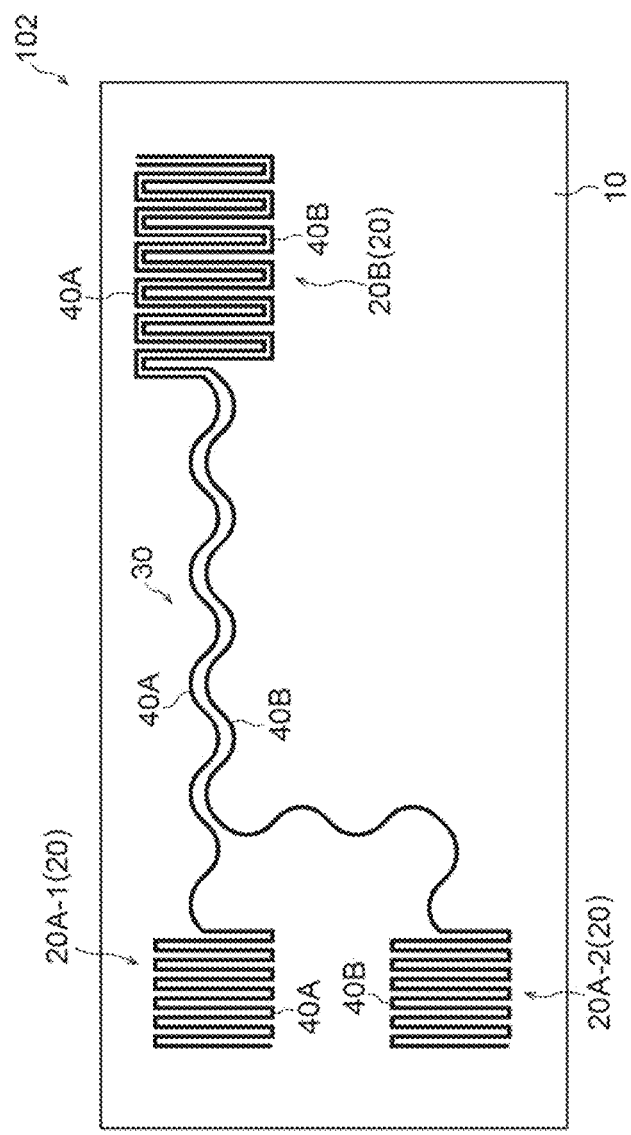
FIG. 7 is a schematic plan view that illustrates a second modification example of the electrode-wiring-equipped cloth material according to the present embodiment.

The electrode-wiring-equipped cloth material 100 according to the present embodiment may also be, for example, an electrode-wiring-equipped cloth material 102 illustrated in FIG. 7. Specifically, as illustrated in FIG. 7, the electrode-wiring-equipped cloth material 100 has electrode sections 20 including plural first electrode sections 20A. It is noted here that, in FIG. 7, as the first electrode sections 20A, a mode of having two electrode sections, which are a first electrode section 20A-1 and a first electrode section 20A-2, is illustrated.

In this mode, for example, a same single conductive linear body 40A is commonly provided in the first electrode section 20A-1, a wiring section 30 and a second electrode section 20B, and a same single conductive linear body 40B is commonly provided in the first electrode section 20A-2, the wiring section 30 and the second electrode section 20B.

(Use)

The electrode-wiring-equipped cloth material 100 can be utilized in wearable devices such as biological signal measuring devices. For example, the electrode-wiring-equipped cloth material 100 to which a prescribed instrument is attached may be cut and processed to obtain a clothing item equipped with a wearable device. Further, the electrode-wiring-equipped cloth material 100 cut to a prescribed size may be attached to a clothing item.

The electrode-wiring-equipped cloth material 100 can also be utilized in, for example, non-wearable biological devices that are not for wearing (e.g., sensors), carpets, curtains, cushion covers, bedding textiles, and fabrics of tents and tarps.

EXAMPLES

The disclosure is described more concretely by way of examples thereof. It is noted here, however, that the following examples do not restrict the disclosure at any rate.

Example 1

A multi-wall carbon nanotube forest formed on a silicon wafer was prepared. While drawing a ribbon of carbon nanotubes from a side surface of the carbon nanotube forest, the ribbon was twisted to obtain a carbon nanotube yarn of 30 µm in diameter. Then, eight of this carbon nanotube yarn were twisted together to obtain a single twisted carbon nanotube yarn.

Meanwhile, an elastic yarn (yarn having elasticity) of a polyurethane fiber covered with polyester was, while being stretched, processed into a two-layer cloth material by a knitting method. In the process of knitting this cloth material, the twisted carbon nanotube yarn was knitted between two cloth material layers in a substantially linear form along the cloth knitting direction. The thus formed undulating region where the carbon nanotube yarn was knitted was defined as a wiring section.

Further, at the respective ends of the substantially linearly knitted carbon nanotube yarn in the knitting direction of the cloth material, the same carbon nanotube yarn as the knitted carbon nanotube yarn was knitted on the same surface of the cloth material (surface cloth material layer) in a repeatedly bending manner such that a quadrangular shape was formed. The thus formed quadrangular regions where the carbon nanotube yarn was knitted were each defined as an electrode section for contact with a living body (first electrode section) and an electrode section for instrument connection (second electrode section).

By performing the above-described steps, an electrode-wiring-equipped cloth material (see FIG. 1) was obtained. The thus obtained cloth material had the following properties.

Properties of Electrode-wiring-Equipped Cloth Material

Size of the electrode-wiring-equipped cloth material: 20 mm in width×110 mm in length Thickness of the electrode-wiring-equipped cloth material: about 500 µm Size of the electrode section for instrument connection: 8 mm×8 mm Size of the electrode section for contact with a living body: 8 mm×8 mm Distance between the electrodes connected via the wiring section: 70 mm Example 2

An electrode-wiring-equipped cloth material (see FIG. 1) was obtained in the same manner as in Example 1, except that a silver-plated polyester yarn (ODEX40/2 available from Osaka Electric Industry Co., Ltd.) was used in place of the carbon nanotube yarn.

[Rate of Change in Resistance of Wiring Section]

In accordance with the above-described method, the rate of change in the resistance of the wiring section before and after elongation of each electrode-wiring-equipped cloth material at 50% of a maximum elongation was determined. It is noted here that the elongation was performed for the part between the electrodes connected via the wiring section. The maximum elongation was 56 mm for both of the electrode-wiring-equipped cloth materials prepared in Examples 1 and 2, and the resistance was measured at an elongation of 28 mm, which is 50% of the maximum elongation, and at the maximum elongation to calculate the rate of change in the resistance.

[Evaluation of Durability after Repeated Elongation-Contraction Operations]

Each electrode-wiring-equipped cloth material was subjected to 100,000 repeated operations of elongation to the maximum elongation and subsequent contraction at a reciprocating frequency of 1 Hz, and the resistance value of the wiring section was measured before and after the elongation-contraction operations. As the resistance value of the wiring section, the resistance in a non-elongated state was measured for the value before the repeated elongation-contraction operations, and the resistance of the wiring section at the maximum elongation of the electrode-wiring-equipped cloth material 100 was measured for the value after the repeated elongation-contraction operations. These resistance values of the wiring section were determined by the same method as the one used for determining the rate of change in the resistance of the wiring section 30. Then, the rate of change in the resistance of the wiring section after the elongation-contraction operations with respect to the resistance of the wiring section before the elongation-contraction operations was determined and evaluated based on the following criteria OK: The rate of change in the resistance of the wiring section was ±10% or lower.

NG: The rate of change in the resistance of the wiring section was higher than ±10%.

TABLE 1

| | Rate of change in resistance of wiring section | | Durability after repeated elongation-contraction operations |
| --- | --- | --- | --- |
| | at 50% of maximum elongation (%) | at maximum elongation (%) | |
| Example 1 | 0.27 | 0.28 | OK |
| Example 2 | 0.94 | 2.22 | NG |

In Example 2, the evaluation of durability after the repeated elongation-contraction operations was rated OK up to 50 repeated operations of elongation.

From the results shown above, it is seen that, in the electrode-wiring-equipped cloth material according to the present embodiment, defective connection between the electrode sections and the wiring section caused by repeated deformation can be inhibited.

The description of symbols is provided as below.

10: cloth material main body

10A: surface cloth material layer

10B: back-surface cloth material layer

10C: intermediate cloth material layer

20: electrode section

30: wiring section

40: conductive linear body

100: electrode-wiring-equipped cloth material

101: electrode-wiring-equipped cloth material

102: electrode-wiring-equipped cloth material

The contents of Japanese Patent Application No. 2018-103874 are incorporated herein by reference.

All of the documents, the patent applications, and the technology standards described here are incorporated here by reference.

The invention claimed is:

1. An electrode-wiring-equipped cloth material, comprising:
   a cloth material main body including a conductive linear body, the conductive linear body having a first end, a second end and a central portion, the conductive linear body comprising:
   a planar first electrode section at the first end and a planar second electrode section at the second end, the first and second planar electrodes arranged by repeatedly bending or curving the conductive linear body back on itself to achieve a series of aligned parallel portions of the conductive linear body;
   and
   a wiring section at the central portion of the conductive linear body, the wiring section connecting the first electrode section and the second electrode section.

2. The electrode-wiring-equipped cloth material according to claim 1, which has elasticity.

3. The electrode-wiring-equipped cloth material according to claim 2, wherein, when the electrode-wiring-equipped cloth material is elongated at 50% of a maximum elongation, a ratio of change in resistance of the wiring section is 10% or less with respect to a resistance of the wiring section prior to elongation of the electrode-wiring-equipped cloth material.

4. The electrode-wiring-equipped cloth material according to claim 1, wherein, in at least one of the planar first electrode section and the planar second electrode section, is restrained by a yarn of the cloth material main body.

5. The electrode-wiring-equipped cloth material according to claim 4, wherein the planar first electrode section is woven, knitted or embroidered into the cloth material main body, or the planar first electrode section is sewn on to the cloth material main body.

6. The electrode-wiring-equipped cloth material according to claim 1, wherein the planar first electrode section and the planar second electrode section are provided on the surface of the cloth material main body and the wiring section is provided inside the cloth material main body.

7. The electrode-wiring-equipped cloth material according to claim 6, wherein the planar first electrode section is in contact with a living body.

8. The electrode-wiring-equipped cloth material according to claim 1, wherein, in the wiring section, a part of the conductive linear body is restrained by a yarn of the cloth material main body.

9. The electrode-wiring-equipped cloth material according to claim 8, wherein, in the wiring section is woven, knitted or embroidered into the cloth material main body, or the wiring section is sewn on to the cloth material main body.

10. The electrode-wiring-equipped cloth material according to claim 1, wherein the wiring section is provided inside the cloth material main body.

11. The electrode-wiring-equipped cloth material according to claim 1, wherein the planar first electrode section and the wiring section are comprised of a carbon nanotube yarn.

12. The electrode-wiring-equipped cloth material according to claim 2, wherein, in the planar first electrode section, a part of the conductive linear body is restrained by a yarn of the cloth material main body.

13. The electrode-wiring-equipped cloth material according to claim 3, wherein, in the planar first electrode section, a part of the conductive linear body is restrained by a yarn of the cloth material main body.

14. The electrode-wiring-equipped cloth material according to claim 12, wherein the planar first electrode section is woven, knitted or embroidered into the cloth material main body, or the planar first electrode section is sewn on to the cloth material main body.

15. The electrode-wiring-equipped cloth material according to claim 13, wherein, in the planar first electrode section is woven, knitted or embroidered into the cloth material main body, or the planar first electrode section is sewn on to the cloth material main body.

16. The electrode-wiring-equipped cloth material according to claim 2, wherein the planar first electrode section is provided on the surface of the cloth material main body.

17. The electrode-wiring-equipped cloth material according to claim 3, wherein the planar first electrode section and the planar second electrode section are provided on the surface of the cloth material main body.

18. The electrode-wiring-equipped cloth material according to claim 4, wherein the planar first electrode section is provided on the surface of the cloth material main body.

19. The electrode-wiring-equipped cloth material according to claim 5, wherein the planar first electrode section and the planar second electrode section are provided on the surface of the cloth material main body.

20. The electrode-wiring-equipped cloth material according to claim 16, wherein the planar first electrode section is in contact with a living body.

* * * * *